United States Patent [19]

Kahan

[11] 4,031,231

[45] June 21, 1977

[54] ANTIBACTERIAL COMPOSITION COMPRISING 3-FLUORO-D-ALANINE OR DEUTERO ANALOG IN COMBINATION WITH AUTO-ANTAGONIST INHIBITOR

[75] Inventor: Frederick M. Kahan, Rahway, N.J.

[73] Assignee: Merck & Co., Inc., Rahway, N.J.

[22] Filed: Jan. 23, 1976

[21] Appl. No.: 651,878

Related U.S. Application Data

[63] Continuation-in-part of Ser. No. 478,793, June 13, 1974, abandoned, which is a continuation-in-part of Ser. No. 387,571, Aug. 10, 1973, abandoned, which is a continuation-in-part of Ser. Nos. 314,878, Dec. 13, 1972, abandoned, and Ser. No. 223,360, Feb. 3, 1972, abandoned.

[52] U.S. Cl. .................................. 424/272; 424/319

[51] Int. Cl.$^2$ ................ A61U 31/42; A61U 31/195
[58] Field of Search ............................ 424/319, 272

*Primary Examiner*—Stanley J. Friedman
*Attorney, Agent, or Firm*—Hesna J. Pfeiffer; Julian S. Levitt

[57] ABSTRACT

Novel antibacterial compositions are prepared by combining 3-fluoro-D-alanine-type compound, such as 3-fluoro-D-alanine and its deutero analogs, and salts and esters thereof, with a 3-fluoro-D-alanine autoantagonist-inhibitor such as cycloserine-type compound. The compositions demonstrate highly effective antibacterial action at high levels of dosage of the 3-fluoro-D-alanine component and, in addition, possess a remarkable synergistic antibacterial action.

15 Claims, No Drawings

ANTIBACTERIAL COMPOSITION COMPRISING 3-FLUORO-D-ALANINE OR DEUTERO ANALOG IN COMBINATION WITH AUTO-ANTAGONIST INHIBITOR

CROSS-REFERENCE TO RELATED APPLICATIONS

This is a continuation-in-part application of copending application U.S. Ser. No. 478,793, filed June 13, 1974 now abandoned, which is a continuation-in-part of copending application U.S. Ser. No. 387,571, filed Aug. 10, 1973 now abandoned, which was a continuation-in-part of applications U.S. Ser. No. 314,878, filed Dec. 13, 1972, abandoned, and U.S. Ser. No. 223,360, filed Feb. 3, 1972, abandoned.

This invention is concerned generally with novel compositions having antibacterial activity. More particularly, it relates to compositions containing a 3-fluoro-D-alanine-type compound in combination with a 3-fluoro-D-alanine autoantagonist-inhibitor, which compositions are characterized as demonstrating, even at greatly elevated concentrations, the highly effective antibacterial action of 3-fluoro-D-alanine-type compounds, and are further characterized as showing a remarkable synergistic action, the antibacterial potency of the combination being substantially in excess of that contributed by the individual components.

The 3-fluoro-D-alanine-type compounds, such as 3-fluoro-D-alanine per se and its deutero analogs, and lower alkyl esters and pharmacologically acceptable salts thereof, are valuable antibacterial agents showing effective activity in inhibiting the growth of pathogenic bacteria of both gram-positive and gram-negative genera, including Streptococcus, Escherichia, Staphylococcus, Pseudomonas, Diplococcus, Klebsiella, Proteus, Mycobacterium, Serratia, Vibrio and Pasteurella, and in particular, bacteria belonging to the species *Escherichia coli, Proteus vulgaris, Proteus mirabilis, Proteus morganii, Streptomyces pyogenes, Pseudomonas aeruginosa, Staphylococcus aureus* and *Aerobacter aerogenes*.

3-fluoro-D-alanine-type compounds do, however, possess the unusual characteristic of being autoantagonists at high concentration, which characteristic is disadvantageous where it is desired to employ the antibacterial at elevated dosages, or where high, autoantogonist concentrations of the 3-fluoro-D-alanine-type compound could result during therapy as, for example, in patients with diminished renal function. Indeed, since elevated dosages of 3-fluoro-D-alanine-type compounds may be employed with safety, it is advantageous in treatment of infections to utilize the 3-fluoro-D-alanine-type compound at a sufficiently high dosage to provide effective antibacterial action against the most resistant organism by which the infection may be caused, at which high dosage the 3-fluoro-D-alanine-type compound is an autoantagonist with respect to more sensitive microorganisms which may be present.

It is now discovered, in accordance with the present invention, that this autoantagonist action shown by 3-fluoro-D-alanine-type compounds at elevated concentration can be completely suppressed by certain substances which are hereinafter referred to as FDA-autoantagonist-inhibitors. As FDA-autoantagonist-inhibitors, it is preferred to employ cycloserine-type compounds such as D-cycloserine per se (hereinafter referred to as cycloserine), terizidone, D-cis-cyclothreonine, D-trans-cyclothreonine, and pharmacologically acceptable salts of cycloserine, terizidone and D-cis(or trans)-cyclothreonine; and N-substituted cycloserine compounds represented by the following formula:

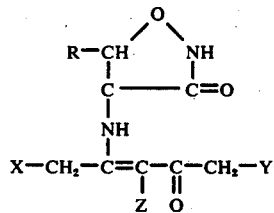

wherein R is hydrogen or methyl, and X, Y and Z are hydrogen or loweralkyl, of 1–6 carbon atoms, and pharmacologicaly acceptable salts thereof, and which may be referred to as D-4-(1'-methyl-3'-oxo-1'-butenyl or alkyl-substituted-1'-methyl-3'-oxo-1'-butenyl-)amino-3-isoxazolidinones, and their 5-methyl derivatives, as for example D-4-(1'-methyl-3'-oxo-1'-butenyl)amino-3-isoxazolidinone, D-4-(1'-methyl-3'-oxo-1'-butenyl)amino-5-methyl-3-isoxazolidinone, D-4-(1',2'-dimethyl-3'-oxo-1'-butenyl)amino-3-isoxazolidinone, D-4-(1',2'-dimethyl-3'-oxo-1'-butenyl)amino-5-methyl-3-isoxazolidinone, D-4-(1'-ethyl-3'-oxo-1'-butenyl)amino-3-isoxazolidinone, D-4-(1'-ethyl-3'-oxo-1'-butenyl)amino-5-methyl-3-isoxazolidinone, D-4-(1'-ethyl-2'-methyl-3'-oxo-1'-butenyl)amino-3-isoxazolidinone, D-4-(1'-ethyl-2'-methyl-3'-oxo-1'-butenyl)amino-5-methyl-3-isoxazolidinone, D-4-(1'-ethyl-3'-oxo-1'-pentenyl)amino-3-isoxazolidinone, D-4-(1'-ethyl-3'-oxo-1'-pentenyl)amino-5-methyl-3-isoxazolidinone, D-4-(1'-ethyl-2'-methyl-3'-oxo-1'-pentenyl)amino-3-isoxazolidinone, D-4-(1'-ethyl-2'-methyl-3'-oxo-1'-pentenyl)amino-5-methyl-3-isoxazolidinone, and the like; pharmacologically acceptable salts of the foregoing such as alkali metal salts, preferably the sodium and potassium salts; alkaline earth metal salts preferably the calcium and magnesium salts; ammonium salts; amine salts, preferably salts with triethylamine, diethylamine, N-methyl-glucamine, diethanolamine, triethanolamine or 2-amino-2-hydroxymethyl-1,3-propanediol, and the like, as for example, the sodium salt of D-4-(1'-methyl-3'-oxo-1'-butenyl)amino-3-isoxazolidinone, the calcium salt of D-4-(1'-methyl-3'-oxo-1'-butenyl)amino-3-isoxazolidinone, the sodium salt of D-4-(1'-methyl-3'-oxo-1'-butenyl)amino-5-methyl-3-isoxazolidinone, and the like; compounds which in vivo liberate cycloserine or methyl-cycloserine, i.e. cyclothreonine, as well as compounds which liberate cycloserine or methyl-cycloserine merely upon solution in aqueous media; as well as other isoxazolidinone compounds which can be characterized in that they themselves, or the products liberated therefrom in vivo or upon solution in aqueous media, have the ability to inhibit the action of the D-alanyl-D-alanine synthetase and/or the D-alanine: α-keto-glutarate transaminase enzymes of microorganisms. It is ordinarily preferred to utilize these N-(1-methyl-3-oxo-1-butenyl or alkyl-substituted-1-methyl-oxo-1-butenyl) derivatives of cycloserine and methyl-cycloserine and their pharmacologically acceptable salts as FDA-autoantagonist-inhibitors, since these derivatives and, more particularly, D-4-(1'-methyl-3'-oxo-butenyl)amino-3-isoxazolidinone and D-4-(1',2'-dimethyl-3'-oxo-1'- butenyl)amino-3-isoxazolidinone, and their sodium and potassium salts, are remarkably stable in aqueous solution; when administered clinically, they are extremely effective in releasing cycloserine or or methyl-cycloserine in vivo and, at the same time, substantially avoiding the unwanted dimerization of the cycloserine or methyl-cycloserine. The D-4-(1'-methyl-3'-oxo-1'-butenyl) amino-3-isoxazolidinone and its pharmacologically acceptable salts are of particular effectiveness in releasing cycloserine in the blood stream and in the bladder, and are thus of value in providing FDA-autoantagonist-inhibitor action throughout the vascular system as well as in the urinary tract.

The critical effectiveness of FDA-autoantagonist-inhibitors is exemplified as follows: 3-fluoro-D-alanine per se, at a concentration of 3.2 µg/ml, completely represses the growth of a virulent culture of *Escherichia coli*, (Strain 2017); however, at higher concentrations (i.e. at 50 µg/ml) extensive growth of the organism occurs characteristic of the autoantagonist action of the 3-fluoro-D-alanine. When the 3-fluoro-D-alanine, at this concentration of 50 µg/ml, is combined with an FDA-autoantagonist-inhibitor, such as cycloserine at concentrations of only 0.39 µg/ml, terizidone at 0.8 µg/ml, D-4-(1'-methyl-3'-oxo-1'-butenyl)amino-3-isoxazolidinone or its sodium salt at 0.72 µg/ml, or D-cis-cyclothreonine at approximately 2 µg/ml, growth of the *Escherichia coli* is completely repressed. Surprisingly, the 0.39 µg/ml cycloserine concentration, completely effective as FDA-autoantagonist-inhibitor, is less than 2% of the minimum concentration of cycloserine (25 µg/ml) which is itself able to completely repress the growth of the *Escherichia coli* organisms: the inhibitor-effective concentrations of terizidone and cyclothreonine are likewise less than 2% of their respective minimum effective antibacterial concentrations.

Moreover, the presently-invented combination of 3-fluoro-D-alanine-type compound with FDA-autoantagonist-inhibitor possesses a remarkable synergistic action, particularly where the FDA-autoantagonist-inhibitor is a cycloserine-type compound, the antibacterial effectiveness of such combination being as much as fifteen times that of the individual components. For example, complete inhibition of the growth of an established culture of *Escherichia coli* (Strain 2017) requires a minimum concentration of 25 µg/ml in the case of cycloserine and 3.12 µg/ml in the case of 3-fluoro-D-alanine, whereas complete inhibition is similarly achieved with a combination containing only 1.56 µg/ml of cycloserine in admixture with 1.56 µg/ml of 3-fluoro-D-alanine, which represents a two-fold reduction in 3-fluoro-D-alanine concentration and over a 15-fold reduction in the concentration of cycloserine.

Cycloserine-type antibacterials, such as cycloserine per se, are used in the treatment of active pulmonary and extra-pulmonary tuberculosis (including renal disease) where the infecting organisms have become resistant to primary medication such as streptomycin and isoniazide, as well as in certain acute urinary tract infections. Their use, even in these critical infections, has been minimal in view of the circumstances that, at the relatively high dosage (greater than 1,000 mg daily) required for therapeutic effectiveness, severe adverse reactions on the nervous system, such as headache, vertigo and convulsions, often occur during therapy. Accordingly, the 15-fold reduction in the cycloserine component, achieved by the foregoing combination containing 1.56 µg/ml of each compound, is of critical importance in view of the adverse reactions encountered with the high dosages of cycloserine ordinarily required in therapy. Thus, the presently invented combination not only makes possible (in view of the contribution of the cycloserine-type component) the utilization of high dosages of 3-fluoro-D-alanine-type compound with complete suppression of autoantagonism, but also (in view of the contribution of 3-fluoro-D-alanine-type component) the utilization of the cycloserine-type compound at a 15-fold reduction in dosage.

This novel combination is conveniently administered for antibacterial effectiveness in the form of a pharmaceutical composition containing the 3-fluoro-D-alanine-type compound in admixture with the FDA-autoantagonist-inhibitor and a pharmacologically acceptable carrier. When a 3-fluoro-D-alanine-type compound is combined with a cycloserine-type compound, the ratio of the 3-fluoro-D-alanine-type component to the cycloserine-type component in the combination ordinarily varies from about 1:120 to about 200:1 with ratios within the range of about 1:4 to about 4:1 being preferred. As the 3-fluoro-D-alanine-type component, it is ordinarily preferred to utilize 3-fluoro-D-alanine, 2-deutero-3-fluoro-D-alanine, 2,3-dideutero-3-fluoro-D-alanine, 2,3,3-trideutero-3-fluoro-D-alanine, a lower alkyl ester thereof such as the methyl ester, or a pharmacologically acceptable salt such as the sodium, calcium, or hydrochloride salt. As the cycloserine-type component, it is ordinarily preferred to utilize cycloserine per se, terizidone, D-cis-cyclothreonine, D-trans-cyclothreonine, or an N-(1-methyl-3-oxo-1-butenyl or alkyl-substituted-1-methyl-3-oxo-1-butenyl) derivative of cycloserine or cyclothreonine, or pharmacologically acceptable salts thereof and it is particularly preferred to employ D-4-(1'-methyl-3'-oxo-1'-butenyl)amino-3-isoxazolidinone, its sodium or potassium salts such as D-4-(1'-methyl-3'-oxo-1'-butenyl)amino-3-isoxazolidinone sodium salt-hemihydrate, or D-4(1',2'-dimethyl-3'-oxo-1'-butenyl)amino-3-isoxazolidinone or its sodium or potassium salts.

Pharmaceutically acceptable carriers for the aforesaid compositions include conventional vehicles adapted for oral administration such as capsules, tablets, or liquid solutions or suspensions, or the combination may be dissolved in a vehicle adapted for administration by injection. Suitable formulations for oral use may include diluents, granulating agents, preservatives, binders, flavoring agents and coating agents which are well known to those skilled in the art, and the dosage of the products may be varied over a wide range. A composition for oral use comprising the combination of 3-fluoro-D-alanine-type compound and cycloserine-type compound is conveniently prepared by intermixing the individual components in a dry, pulverulent state with gelatin, starch, magnesium stearate and alginic acid, pressed into a tablet. The 3-fluoro-D-alanine-type compound and the cycloserine-type compound may also be incorporated together in aqueous solution, and the solution evaporated to provide the combination in the form of an intimate mixture of the components.

Alternatively, in accordance with a further embodiment of this invention, the components of the combination may be separately administered, particularly where it is desired for maintenance of blood levels of the more rapidly excreted 3-fluoro-D-alanine-type component.

Experimental studies, which illustrate the effectiveness of the presently-invented combination in the treatment of infections in living animals, are set forth in the following examples, but it is to be understood that these examples are given for purposes of illustration and not of limitation.

EXAMPLE 1

Female C.D.1 mice of average weight 21.0 g. are injected intraperitoneally with 0.5 ml. of an appropriate dilution of a 16-hour broth culture containing the indicated pathogen. (The severity of the infectious challenge is represented in each case as the multiple of the dilution of the broth culture which is lethal for only 50% of the untreated population, i.e. No. $LD_{50}$.) Appropriate dosages of 3-fluoro-D-alanine (FDA) and D-cycloserine, individually, and combinations of these two components in a fixed ration of 1:1 are administered in 0.5 ml volume subcutaneously on the dorsal surface, promptly at the time of the injection, and at 2 hour and 4 hour intervals thereafter. The results of these tests, which are expressed as the $ED_{50}$ dose, which is the statistically interpolated dose required to protect 50% of the infected population for a period of 7 days following challenge and treatment, are as follows:

| Infecting Organism | No. $LD_{50}$ | $ED_{50}$ mg/dose at 0, 2, 4 Hours | | |
|---|---|---|---|---|
| | | Individual Components | | Combination |
| | | FDA | cycloserine | FDA + cycloserine |
| Staphylococcus aureus 2949 | 30 | 0.801 | 0.400 | 0.035 + 0.035 |
| Proteus morganii 3376 | >100 | >2.0 | >5.0 | 0.57 + 0.57 |
| Serratia species 3374 | 3 | 1.7 | 2.5 | 0.18 + 0.18 |

The reduction in dosage for the FDA-cycloserine combination, as compared with that for the individual components, is as follows:

| Infecting organism | $ED_{50}$ For Combination Expressed As Approximate Percentage of $ED_{50}$ For Individual Components | |
|---|---|---|
| | FDA | Cycloserine |
| Staphylococcus aureus | 5% | 9% |
| Proteus Proteus <25% | <10% | |
| Serratia species | 10% | 7% |

EXAMPLE 2

Groups of five female C.D.1 mice of average weight 21.0 g are injected intraperitoneally with 0.5 ml of a diluted broth culture of *Escherichia coli* 2017 representing 3 $LD_{50}$ of bacterial pathogens. The indicated dosages of 3-fluoro-D-alanine (FDA) and D-cycloserine are then promptly administered in a 0.5 ml volume by the subcutaneous route on the dorsal surface.

Across the top row of the tabulation are listed the number of mice surviving (in each group of five infected mice) for the indicated doses (mg) of 3-fluoro-D-alanine alone; in the first vertical column are listed the number surviving for the indicated doses (mg) of cycloserine alone; and in the second vertical column are listed the number of mice surviving for combination doses of 5.0 mg of 3-fluoro-D-alanine and the indicated amount (mg) of cycloserine.

| Mg D-Cycloserine per dose | NUMBER OF SURVIVORS IN EACH GROUP OF FIVE INFECTED MICE | | | | |
|---|---|---|---|---|---|
| | Mg of 3-Fluoro-D-Alanine per dose | | | | |
| | 0 | 0.078 mg | 0.312 mg | 1.25 mg | 5.0 mg |
| 0 | 0 | 0 | 3 | 4 | 1 |
| 0.019 mg. | — | | | | 0 |
| 0.039 mg | — | | | | 1 |
| 0.078 mg | 0 | | | | 2 |
| 0.156 mg | — | | | | 5 |
| 0.312 mg | 0 | | | | 5 |
| 0.625 mg | — | | | | 5 |
| 1.25 mg | 3 | | | | 5 |
| 2.5 mg | — | | | | 5 |
| 5.0 mg | 5 | | | | 5 |

It will be noted that a 1.25 mg dose of 3-fluoro-D-alanine alone gives an 80% survival whereas a 5.0 mg dose (due to autoantagonism) gives only a 20% survival. A combination dose of 5.0 mg of 3-fluoro-D-alanine and 0.156 mg of cycloserine (at which level cycloserine alone results in zero protection) gives 100% survival, i.e. the 0.156 mg of cycloserine completely suppresses the autoantagonism shown by 3-fluoro-D-alanine at the 5.0 mg dosage level.

The N-(1-methyl-3-oxo-1-butenyl or alkyl-substituted-1-methyl-3-oxo-1-butenyl) cycloserine or methylcycloserine 3-FDA-autoantagonist inhibitors may be prepared by stirring together, at room temperature for a period of about 2 days, cycloserine or methylcycloserine with an excess of a 2,4-pentanedione compound having the following formula:

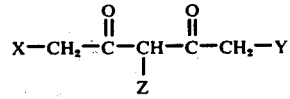

wherein X, Y and Z are hydrogen or alkyl, such as 2,4-pentanedione, under which conditions, the cycloserine compound gradually goes into solution, with formation of the corresponding N-substituted-cycloserine compound of the formula:

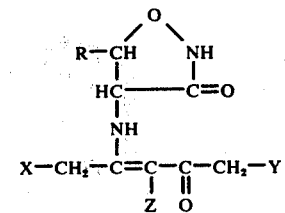

wherein R is hydrogen or methyl, and X, Y and Z are hydrogen or alkyl, which, as the reaction proceeds, crystallizes from the resulting reaction solution, and is recovered by filtration, washed with ether and dried. For example, D-4-(1'-methyl-3'-oxo-1'-butenyl)amino-3-isoxazolidinone is conveniently prepared by stirring a mixture of about 3.0 g. of D-4-amino-3-isoxazolidinone and 30 ml. of 2,4-pentanedione in a dry atmosphere at approximately room temperature for about 2 days. The D-4-amino-3-isoxazolidinone gradually goes into solution, and the reaction product, which crystallizes from the reaction solution, is recovered by filtration, washed with three 20 ml.-portions of ether, and dried at room temperature in vacuo to give about 3.5 g. of D-4-(1'-methyl-3'-oxo-1'-butenyl)amino-3-isoxazolidinone.

The latter is conveniently converted to its pharmacologically acceptable salts, e.g. the sodium or calcium salts as follows: 0.143 g. of D-4-(1'-methyl-3'-oxo-1'-butenyl)amino-3-isoxazolidinone is dissolved in 0.8 ml. of methanol, and 1.56 ml. of an 0.05 molar solution of sodium hydroxide in methanol, is added to give a pH of approximately 7.0. The methanol is evaporated from the resulting solution under a stream of nitrogen until crystals form; the crystalline slurry is further evaporated to dryness in vacuo. The residual material is washed with 2.5 ml. of acetone, and redissolved in 0.55 ml. of methanol; the solution is filtered and the filtrate diluted with 0.45 ml. of methanol. To the resulting solution is added 4 ml. of ether, and the crystalline precipitate which forms is recovered by filtration, washed with ether and dried to give substantially pure D-4-(1'-methyl-3'-oxo-1'-butenyl)amino-3-isoxazolidinone sodium salt-hemihydrate.

Three grams of calcium oxide are slurried in 40 ml. of water, and the slurry cooled to 0–5° C. Five grams of D-4-(1'-methyl-3'-oxo-1'-butenyl)amino-3-isoxazolidinone is added to the cooled slurry, the resulting mixture is heated with slurry to room temperature and stirred at that temperature for 5 minutes. The mixture is filtered, and the insoluble material is washed with 10 ml. of water. To the combined solution and washings (having a pH of about 11.0 - 11.5) is added sufficient D-4-(1'-methyl-3'-oxo-1'-butenyl)amino-3-isoxazolidinone to give a final pH of about 9.5. Activated carbon (0.5 g.) is added to the resulting solution, and the mixture is stirred for about 15 minutes and filtered. The filtered solution is diluted with six times its volume of ethanol, and the crystalline precipitate which forms is recovered by filtration, washed with ethanol and dried in vacuo to give, in substantially pure form, the calcium salt of D-4-(1'-methyl-3'-oxo-1'-butenyl) amino-3-isoxazolidinone.

Various changes and modifications may be made in carrying out the present invention without departing from the spirit and scope thereof. Insofar as these changes and modifications are within the purview of the annexed claims, they are to be considered as part of this invention.

What is claimed is:

1. An antibacterial composition comprising as active ingredients a combination of 3-fluoro-D-alanine-type compound and 3-fluoro-D-alanine autoantagonist-inhibitor characterized in that the 3-fluoro-D-alanine-type compound is selected from the group consisting of 3-fluoro-D-alanine, 2-deutero-3-fluoro-D-alanine, 2,3-dideutero-3-fluoro-D-alanine, 2,3,3-trideutero-3-fluoro-D-alanine, and their lower alkyl ester or pharmacologically acceptable salt thereof; and the 3-fluoro-D-alanine autoantagonist inhibitor is cycloserine, terizidone, cis-cyclothreonine, transcyclothreonine or an N-substituted cycloserine compound having the formula

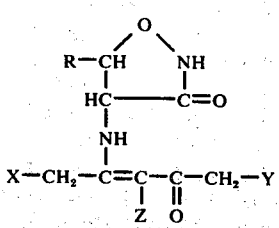

wherein R is hydrogen or methyl, and X, Y, and Z are hydrogen or loweralkyl, or pharmacologically acceptable salts thereof, the ratio of the 3-fluoro-D-alanine-type compound to the autoantagonist inhibitor being within the range of about 1:120 to about 200:1.

2. A composition as defined in claim 1 in which said combination is in admixture with a pharmaceutical carrier.

3. A composition as defined in claim 2 wherein the pharmaceutical carrier is adapted for oral administration.

4. A composition as defined in claim 1 in which the 3-fluoro-D-alanine-type compound is 3-fluoro-D-alanine or pharmacologically acceptable salt thereof, and the 3-fluoro-D-alanine autoantagonist-inhibitor is D-4-(1'-methyl-3'-oxo-1'-butenyl)amino-3-isoxazolidinone or a pharmacologically acceptable salt thereof.

5. A composition as defined in claim 1 in which the 3-fluoro-D-alanine-type compound is 2-deutero-3-fluoro-D-alanine, and the 3-fluoro-D-alanine autoantagonist-inhibitor is D-4-(1'-methyl-3'-oxo-1'-butenyl)amino-3-isoxazolidinone.

6. A composition as defined in claim 1 in which the 3-fluoro-D-alanine-type compound is 2-deutero-3-fluoro-D-alanine or pharmacologically acceptable salt thereof, and the 3-fluoro-D-alanine autoantagonist-inhibitor is D-4-(1',2'-dimethyl-3'-oxo-1'-butenyl)-amino-3-isoxazolidinone or pharmacologically acceptable salt thereof.

7. A composition as defined in claim 1 in which the 3-fluoro-D-alanine-type compound is 3-fluoro-D-alanine or pharmacologically acceptable salt thereof, and the 3-fluoro-D-alanine autoantagonist-inhibitor is D-cycloserine.

8. A composition as defined in claim 1 in which the 3-fluoro-D-alanine-type compound is 2-deutero-3-fluoro-D-alanine or pharmaceutically acceptable salt thereof, and the 3-fluoro-D-alanine autoantagonist-inhibitor is D-cycloserine.

9. A composition as defined in claim 1 in which the 3-fluoro-D-alanine-type compound is 3-fluoro-D-alanine or pharmacologically acceptable salt thereof, and the 3-fluoro-D-alanine autoantagonist-inhibitor is terizidone.

10. An antibacterial composition comprising as active ingredients a combination of 3-fluoro-D-alanine-type compound and 3-fluoro-D-alanine autoantagonist-inhibitor characterized in that the 3-fluoro-D-alanine-type compound is selected from the group consisting of 3-fluoro-D-alanine, 2-deutero-3-fluoro-D-alanine, 2,3-dideutero-3-fluoro-D-alanine, 2,3,3-trideutero-3-fluoro-D-alanine and their loweralkyl ester and pharmacologically acceptable salt thereof; and the 3-fluoro-D-alanine autoantagonist inhibitor is an isoxazolidinone compound which, in vivo or upon solution is aqueous media, has the ability to inhibit the action of the D-alanyl-D-alanine synthetase or D-alanine: α-keto-glutarate transaminase enzymes of microorganisms, the ratio of the 3-fluoro-D-alanine-type compound to the autoantagonist inhibitor being within the range of about 1:120 to about 200:1.

11. The composition of claim 10 in which said combination is in admixture with a pharmaceutical carrier.

12. The composition of claim 11 in which the pharmaceutical carrier is adapted for oral administration.

13. An antibacterial composition comprising 2-deutero-3-fluoro-D-alanine and D-4-(1'-methyl-3'-oxo-1'-butenyl)amino-3-isoxazolidinone, sodium salt, the ratio of the alanine compound to the isoxazolidinone compound being within the range of about 1:4 to 4:1.

14. An antibacterial composition comprising 3-fluoro-D-alanine and D-4-(1'-methyl-3'-oxo-1'-butenyl)-amino-3-isoxazolidinone, sodium salt, the ratio of the alanine compound to the isoxazolidinone compound being within the range of about 1:4 to 4:1.

15. An antibacterial composition comprising either 2-deutero-3-fluoro-D-alanine or 3-fluoro-D-alanine and D-cycloserine or a pharmacologically acceptable salt thereof, the ratio of the alanine compound to the cycloserine compound being within the range of about 1:4 to 4:1.

* * * * *